Feb. 6, 1973

Re. 27,569

B. ACKERMAN

CARDIAC CATHETERIZATION APPARATUS AND METHOD

Filed Aug. 16, 1965

INVENTOR.
BERNARD ACKERMAN

BY LACKENBACH & SIEGEL

ATTORNEYS

United States Patent Office

Re. 27,569
Reissued Feb. 6, 1973

27,569

CARDIAC ELECTRODE CATHETER AND HEART STIMULATION METHOD

Bernard Ackerman, Metuchen, N.J., assignor to Electro-Catheter Corporation, Rahway, N.J.

Original No. 3,485,247, dated Dec. 23, 1969, Ser. No. 480,020, Aug. 16, 1965. Application for reissue Aug. 27, 1970, Ser. No. 67,406
Int. Cl. A61n *1/04*
U.S. Cl. 128—418 14 Claims

Matter enclosed in heavy brackets [ ] appears in the original patent but forms no part of this reissue specification; matter printed in italics indicates the additions made by reissue.

ABSTRACT OF THE DISCLOSURE

A bipolar catheter includes an outer conductor and an inner conductor located inside the outer conductor and insulated therefrom except at the outermost portion. The outer conductor is divided intermediate its length and the two portions from the terminals of the catheter. The catheter is inserted in the heart by puncturing the patient's chest wall and heart with a needle and threading the catheter therethrough, after which the needle is removed and the catheter is connected to a suitable electrical impulse generator.

The present invention pertains, generally, to cardiac apparatus or devices and methods of utilization thereof, and, more particularly, to cardiac apparatus or devices that are constructed and arranged to effectively artifically stimulate the heart in an unusually efficient manner, and with the greatest of ease and to methods thereof.

Cardiac arrest is a situation in which the heart has simply stopped beating, and the person is ostensibly dead. Reasons for the heart ceasing to function are many, for example, accident, electrocution, poisoning, shock, and the like. Cardiac devices are presently available for artificially stimulating the stopped heart and thus resuscitating a person or individual. Similarly, prescribed procedures for artificially stimulating the heart in an instance of cardiac arrest are also presently known. As is considered readily apparent, time is a critical factor. Thus, the user must be able to effect the necessary procedure with extreme facility, with the expenditure of a minimal amount of effort, all in the least possible time. It has been found that presently available cardiac apparatus or devices are not capable of entirely satisfying these criteria.

Having in mind each and every one of the foregoing disadvantages, and others that will readily be apparent to those skilled in the art, it is a primary object of the present invention to provide cardiac apparatus for resuscitating an individual who ostensibly is dead because his heart has ceased to beat, said cardiac apparatus being constructed and arranged to be capable of use with great facility for artificially stimulating the stopped heart in an unusually efficient maner, and with the expenditure of a minimal amount of time.

Another primary object of this invention, in addition to the foregoing objects, is to provide cardiac apparatus for resuscitating a person who ostensibly is dead because his heart has ceased to beat, said cardiac apparatus being constructed and arranged to present more than an adequate degree of flexibility and resiliency, enabling free movement of the heart, and the maintenance of electrical contact therewith, all without the possibility of damage thereto, further enabling said cardiac apparatus to be handled with great facility for artifically stimulating a stopped heart in an unusually efficient manner, and with the expenditure of a minimal amount of time.

Yet another primary object of the present invention, in addition to each and every one of the foregoing objects, is to provide cardiac apparatus for resuscitating a person who ostensibly is dead because his heart has ceased to beat, said cardiac apparatus being constructed and arranged to present more than a sufficient degree of flexibility and resiliency, enabling freedom of movement of the heart, and maintenance of electrical contact therewith, without introducing the possibility of damage thereto, and being further constructed and arranged to be capable of defining an electrical circuit in and of itself for transmitting electrical impulses to the heart without requiring the use of any additional or extraneous implementation other than an impulse generator for approximating the normal current of the heart in strength, frequency and distribution.

A further primary object of this invention, in addition to each and every one of the foregoing objects, is to provide a bi-polar flexible and resilient cardiac apparatus for resuscitating a person who ostensibly is dead because his heart has ceased to beat by artificially stimulating the heart in an unusually efficient and facile manner, while yet requiring the expenditure of a minimal amount of time, said cardiac apparatus being constructed and arranged to remain in contact with the heart for long periods of time, if necessary, while yet providing maximum comfort to the patient.

A still further object of the present invention, in addition to each and every one of the foregoing objects, is to provide bi-polar flexible and resilient cardiac apparatus for resuscitating a person who ostensibly is dead because his heart has ceased to beat by artificially stimulating the heart in an unusually efficient and facile manner, while yet requiring the expenditure of a minimal amount of time, said cardiac apparatus being constructed and arranged to be very light, compact and portable, capable of being carried about by a physician as part of emergency kit, or stored in emergency cabinets in hospitals or similar institutions, or made a part of emergency apparatus in general.

Moreover, it is a primary object of this invention, in addition, to each and every one of the foregoing objects, to provide bi-polar flexible and resilient cardiac apparatus for resuscitating a person who ostensibly is dead because his heart has ceased to beat by artificially stimulating the heart in an unusually efficient and facile manner, while yet requiring the expenditure of a minimal amount of time, said cardiac apparatus being constructed and arranged to be sturdy and durable, and capable of being relied upon to perform at all times and under any circumstances.

It is another primary object of the present invention, in addition to each and every one of the foregoing objects, to provide bi-polar flexible and resilient cardiac apparatus for resuscitating a person who ostensibly is dead because his heart has ceased to beat by artificially stimulating the heart in an unusually efficient and facile manner, while yet requiring the expenditure of a minimal amount of time, said cardiac apparatus being constructed and arranged of relatively few and simple parts, enabling said apparatus to be fabricated economically.

Yet still another primary object of the present invention, in addition to each and every one of the foregoing objects, is to provide novel methods of cardiac catheterization.

Another and yet still further primary object of the present invention, in addition to each and every one of the foregoing objects, is to provide novel methods for artificially stimulating muscular tissues, such as cardiac tissues.

Other objects and important features of the present invention will be apparent from a study of the specification following taken with the drawings, which together show, illustrate, describe and disclose at least one preferred embodiment or modification of the invention, and what is now considered to be the best mode of practicing the principles thereof. Other embodiments or modifications may be suggested to those having the benefits of the teachings herein, and such other embodiments or modifications are intended to be reserved especially as they fall within the scope and spirit of the sub-joined claims.

Figure 1:
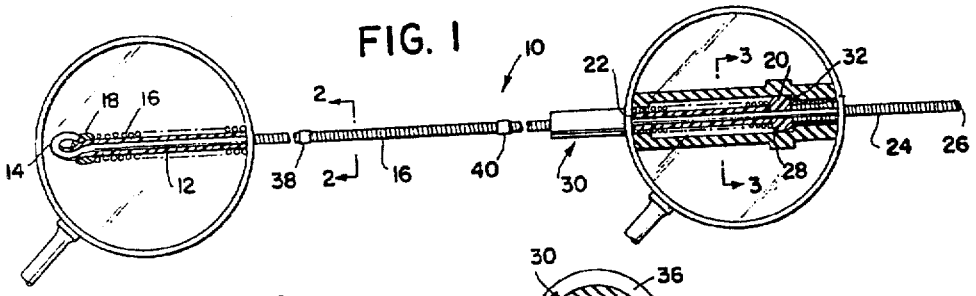
FIG. 1 is an elevational view, partially in section and drawn to an enlarged scale, of one embodiment of cardiac apparatus constructed in accordance with the principles of the present invention.

With reference now to the drawings, and particularly to FIG. 1, there is illustrated therein one embodiment of cardiac apparatus constructed in accordance with the principles of the present invention, and generally designated by the reference character 10.

The cardiac apparatus or device 10 comprises a first or inner electrode 12 that terminates at one end thereof or at the tip in a hook or loop 14. The inner electrode 12 may be fabricated of any suitable electrically conductive material. The cardiac apparatus or device 10 further comprises a second, outer or peripheral electrode 16. This electrode also is fabricated of a suitable electrically conductive material, and preferably takes the form of an extremely flexible and resilient coil spring, the coils of which are positioned close to or immediately adjacent one another.

The inner and outer electrodes 12 and 16, respectively, are fixed or joined to one another at a joint 18 to preclude relative movement therebetween. The joint 18 may be fabricated of any suitable dielectrical or non-conductive material, as, for example, an epoxy resin.

The inner electrode 12 is of greater length than the outer electrode 16, the latter terminating at a location or region 20 remote from the tip 14. An insulating tube 22 that is fabricated of a suitable dielectric material is positioned between the electrodes 12 and 16, and extends from the tip 14 to the location or region 20. As is considered readily apparent, the insulating tube 22 precludes shorting of the electrode between the tip 14 and the region 20 at any location therebetween. This is important since, as will hereinafter more fully be described, the myocardium and the outer electrode 16 define one path of an electrical circuit.

The cardiac apparatus 10 further comprises an auxiliary outer electrode 24 that extends substantially from the location of region 20 to a distal end 26, at which the inner electrode 12 also terminates. The outer electrode 16 and the auxiliary outer electrode 24 are affixed or secured to one another at the location or region 20 by a joint 28 that may be fabricated of any suitable dielectric or non-conductive material, such as, again, an epoxy resin. Accordingly, relative movement between the inner electrode 12 and the outer electrode 16 is precluded at the region 20, as it is at the tip 14. Relative movement is also precluded between the inner electrode 12 and the auxiliary outer electrode 24, and also between the latter and the outer electrode 16.

The cardiac apparatus 10 further comprises a tubular movable sleeve 30 that may be fabricated of any suitable material, such as a plastic, the sleeve 30 is particularly adapted to be disposed at the location or region 20 and about the joint 28 to preclude excessive flexing of the device 10 at this location, and possible damage thereto. To properly locate the sleeve 30, it is recessed interiorly thereof to define a shoulder 32 that is particularly adapted to be disposed in abutting engagement with the joint 28. To facilitate movement of the sleeve 30 longitudinally or axially of the cardiac apparatus, the sleeve comprises an annular collar 34 extending completely peripherally thereabout.

Still further, the cardiac apparatus or device 10 comprises a first or primary marker 38 and a secondary or auxiliary marker 40, for a purpose that will hereinafter more fully be described. The markers 38 and 40 may be fabricated of any suitable material, and are affixed to the outer electrode 16 in any suitable manner.

Figure 4:
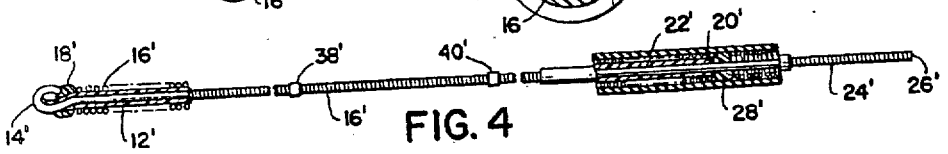
FIG. 4 is an elevational view, partially in section and drawn to an enlarged scale, of another embodiment of cardiac apparatus constructed in accordance with the principles of the present invention.
Figure 5:
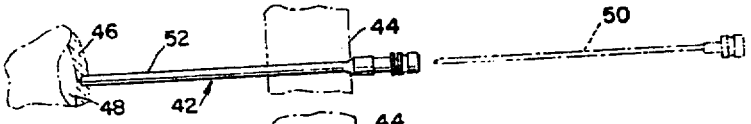
FIG. 5 is an elevational view of the embodiment shown in FIG. 4, illustrating the first step in the use of that cardiac apparatus.
Figure 6:
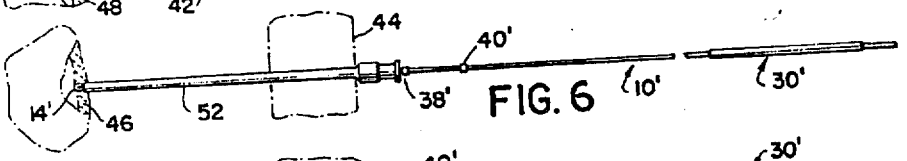
FIG. 6 is a view similar to FIG. 5, illustrating the second step in the use of the cardiac apparatus.
Figure 7:
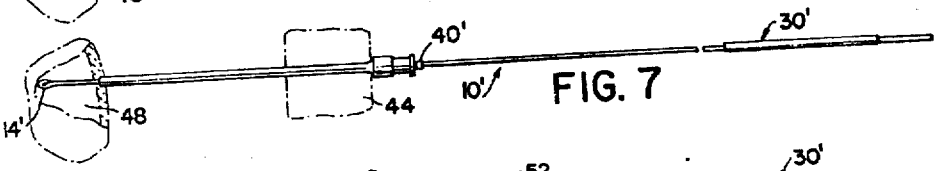
FIG. 7 is a view similar to FIGS. 5 and 6, illustrating the third step in the use of the cardiac apparatus.
Figure 8:
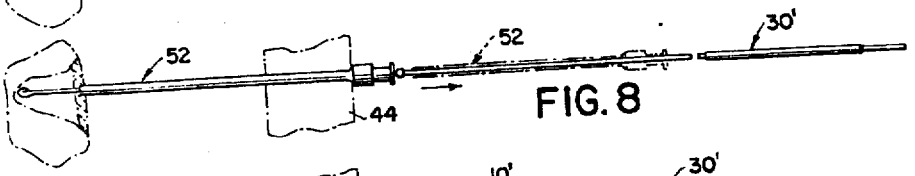
FIG. 8 is a view similar to FIGS. 5–7, illustrating the next step in the use of the cardiac apparatus.
Figure 9:
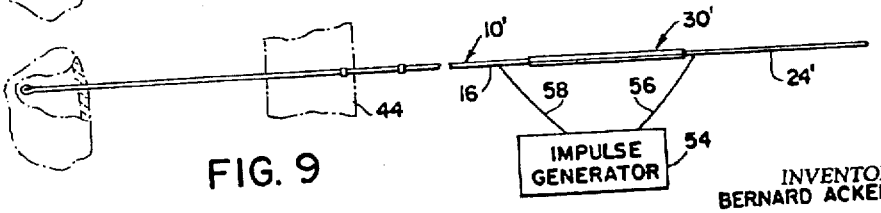
FIG. 9 is a view similar to FIGS. 5–8, illustrating the final step in the use of the cardiac apparatus.

With particular reference now to FIG. 4, wherein like reference characters indicate like parts, but wherein the reference characters are primed, there is illustrated therein another embodiment of cardiac apparatus constructed in accordance with the principles of the present invention, and generally designated by the reference character 10'.

Figure 2:
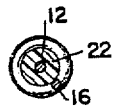
FIG. 2 is a cross-sectional view taken along the line 2—2 of FIG. 1.
Figure 3:
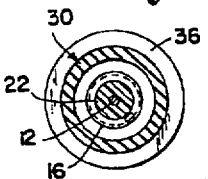
FIG. 3 is a cross-sectional view taken along the line 3—3 of FIG. 1.

The cardiac apparatus or device 10' is substantially the same as the device illustrated in FIGS. 1–3, with the exception that the tubular sleeve 30' is affixed or secured to the other electrode 16' and the auxiliary outer electrode 24' at the location or region 20'. The sleeve 30', again, may be fabricated of any suitable material, and may be affixed or secured to the outer electrodes 16' and 24' in any suitable manner. Since the sleeve is affixed thereto at the location 20', once again excessive flexing at this location is precluded, as is possible damage at this location to the joint 28'. Since the sleeve 30' is affixed or secured to the electrodes 16' and 24', it is of less diametral dimensional extent than the sleeve 30, for reasons that will hereinafter more fully be understood.

A salient feature of the present invention must now be emphasized. In a cardiac device of the present invention, the insulating tube, namely, the tube 22 of the device 10, and the tube 22' of the device 10', extends from the tip 14 or 14' to the location or region 20 or 20', respectively. The tube terminates at the location or region, so that no insulation is present between the inner electrode 12 or 12' and the auxiliary outer electrode 24 or 24', respectively. Accordingly, in a cardiac device of the present invention, the auxiliary outer electrode and the inner electrode are virtually in electrical contact with one another.

Accordingly, current supplied to the auxiliary outer electrode will be transmitted to the inner electrode, and then to the tip of the cardiac device. There is thus defined one path of an electrical circuit. Another path of the electrical circuit will at least comprise the outer electrode 16 or 16'. The presence of the insulating tube 22 or 22' will preclude shorting between the two paths of the electrical circuit at any location between the tip 14 or 14' and the region 20 or 20', respectively. It can be said, therefore, that there is defined a bi-polar cardiac apparatus in that the apparatus in and of itself comprises an electrical circuit. Another salient feature of the present invention is the extreme degree of flexibility and resiliency presented thereby. This is particularly true since the outer electrode and the auxiliary outer electrode are fabricated of coil springs. As a result, cardiac apparatus constructed in accordance with the principles of the present invention will be easy to handle, will provide for freedom of movement of the heart while maintaining electrical contact therewith, and will substantially reduce, if not completely eliminate, the possibility of damage to the tissue and muscle of the heart and body with which the cardiac apparatus is in contact. At the same time, there is presented a cardiac apparatus that is economical of manufacture, while yet being reliable, sturdy and durable in use, even over long periods of time, and repeated utilizations.

Fith particular reference now to FIGS. 5–9, there are illustrated therein the various steps of the procedure for utilizing the cardiac apparatus or device 10' illustrated in FIG. 4.

When an instance of cardiac arrest is diagnosed, a needle 42 of any suitable and conventional construction, approximately 6 inches in length, is inserted through the chest wall 44 substantially at the fourth and fifth intercostal (occurring between the ribs of the torso) space. The needle 42 is then inserted into the ventricular wall 46 until it reaches a location at which it just enters the ventricle or chamber cavity 48. This may be the left ventricle of the heart. Entry to the right ventricle can be made by passing the needle under the sternum, or substernally.

The needle 42 may be of any suitable and conventional construction, as hereinbefore pointed out, and will comprise a needle portion 50 and a sleeve portion 52. The needle portion 50 is now removed, as illustrated in phantom in FIG. 5, and the cardiac apparatus 10' inserted into the sleeve portion 52. The cardiac apparatus is caused to move into the sleeve portion until the primary marker 38' is adjacent the hub of the sleeve portion. When the primary marker is disposed at this location, the tip 14' will just have emerged from the sleeve portion 52, and, therefore, will have just entered the ventricular wall 46. This is true since the distance between the tip 14' and the primary marker 38' is chosen to be substantially the same as the distance between the tip and the hub of the sleeve portion 52. Accordingly, the user can follow the progress of the cardiac apparatus through the sleeve portion, and maintain a check on the tip 14'. In particular, the user can determine when the tip just emerges from the needle portion at the ventricular wall 46.

The distance between the primary and secondary markers 38' and 40', respectively, is generally arbitrarily chosen. However, the distance between these markers is chosen to dispose the tip 14' of the apparatus 10' a sufficient distance into the ventricular cavity 48 when the auxiliary marker 40' is positioned adjacent the hub of the sleeve portion 52. It can also be said that movement of the apparatus 10' continues until contact with the endocardium (not shown) in the ventricular cavity is felt.

The cardiac apparatus 10' is now grasped or held at a location remote from the chest wall 44, enabling the sleeve portion 52 to be completely withdrawn therefrom. The cardiac apparatus 10' is then grasped near the surface of the chest wall 44, enabling the sleeve portion 52 to be slipped off of the apparatus or device. This can be accomplished with facility since the diameter of the sleeve 30' is slightly less than the interior diameter of the sleeve portion.

An impulse generator 54 is now connected to the cardiac apparatus or device 10' across the sleeve 30'. The impulse generator 54 may be of any suitable and conventional construction capable of delivering an electric current approximating in strength, frequency and distribution the normal current of the heart. The cardiac apparatus or device 10', as hereinbefore pointed out, is bi-polar in that it defines a complete electric circuit, with the exception of a source of energy, in and of itself. Accordingly, connecting the impulse generator 54 to the auxiliary outer electrode 24' by a lead 56 will transmit current to the inner electrode 12', since no dielectric material is disposed therebetween. The impulses generated by the generator 54 will thus be transmitted to the tip 14', and thence to the tissue of the heart. The heart tissues are electrically conductive, so that the impulses received thereby will be transmitted to the outer electrode 16', and thence returned to the impulse generator 54 by a lead 58.

The procedure for utilizing the cardiac apparatus or device 10 is substantially the same as that just described, with the exception that the sleeve 30 must first be removed before removing the sleeve portion 52 of the needle 42. Subsequent to its removal, the sleeve 30 is again positioned upon the cardiac apparatus, and moved to a position at which the shoulder 32 abuts the joint 28, for the reasons and purposes hereinbefore described.

It will now be understood that the hereinbefore described salient features of cardiac apparatus constructed in accordance with the principles of the present invention enable a successful achievement of the object hereinbefore set forth. Thus, by constructing and arranging the inner electrode 12' of an electrically conductive material that is at least flexible, and by constructing and arranging the outer electrodes 16' and 24' of a coil spring, which is resilient as well as flexible, there is provided an extremely flexible and resilient cardiac apparatus for artificially stimulating a heart that has ceased beating in an unusually efficient manner, with extreme facility, and with the expenditure of a minimal amount of time. This flexibility and resiliency is also important in that it enables the cardiac apparatus to follow the motion of the heart, while at the same time substantially reducing, if not completely eliminating, damage and irritation to the tissue of the body. Accordingly, cardiac apparatus of the present invention can be utilized to stimulate the heart for substantial periods of time, and for such periods of time, can be retained in the body without causing discomfort thereto. Moreover, cardiac apparatus of the present invention is bi-polar in that it in and of itself defines a plurality of contacts across which a potential difference may be established for enabling electric impulses to be transmitted through the circuit defined thereby. This is accomplished by constructing and arranging the outer electrode of separate coil springs that are insulated from one another, and insulating one of the outer electrodes from an inner electrode.

In FIG. 1 the tip area and the region 20 of the cardiac apparatus 10 has been drawn to an enlarged scale to facilitate an understanding of the present invention, and, in effect, has been shown as it would appear through a magnifying glass. That element has not been described, however, since it does not comprise a part of the present invention.

While the invention has been shown, illustrated, described and disclosed in terms of embodiments or modifications which it has assumed in practice, the scope of the invention should not be deemed to be limited by the precise embodiments or modifications herein shown, illustrated, described or disclosed, such other embodiments or modifications intended to be reserved especially as they fall within the scope of the claims here appended.

What is claimed is:

1. Bi-polar catheter electrodes for percutaneous application of electrical energy directly to muscular tissues, and particularly for direct cardiac stimulation and pacing, comprising, in combination, an inner electrode fabricated of an electrically conductive flexible material having a tip of hook-shape configuration and a distal end; an outer electrode comprising a coil spring fabricated of an electrically conductive extremely flexible and resilient material, said inner electrode being of greater length than and disposed generally longitudinally within said outer electrode and said outer electrode terminating at a region remote from said tip; an insulating tube fabricated of dielectric material positioned between said inner and outer electrodes and extending from said tip to said region; an auxiliary outer electrode in electrical communication with said inner electrode and comprising a coil spring fabricated of an extremely flexible and resilient material positioned about said inner electrode and extending from said region to said distal end; a joint fabricated of a dielectric material positioned at said region and joining said inner, outer and auxiliary outer electrodes to one another; a sleeve positioned about said outer and auxiliary outer electrodes for protecting the joint at said region by precluding excessive flexing at that location; a plurality of spaced markers positioned upon said outer electrodes; and an impulse generator connected to said outer and said auxiliary outer electrodes across the joint at said region.

2. Catheter electrode defined in claim 1 wherein said sleeve is movable longitudinally of said outer and auxiliary outer electrodes for removal therefrom and comprises an interior recess that defines a shoulder adapted to abut against the joint at said region for precluding movement of the sleeve beyond that location.

3. Catheter electrode defined in claim 1 wherein said sleeve is fixed to said outer and auxiliary outer electrode at said region.

4. Apparatus for conducting electrical energy to muscle tissue for artificial stimulation thereof comprising, in combination, an inner and an outer generally coaxial electrically conductive elements and an insulating element disposed between said inner and said outer electrically conductive elements, said insulating element terminating at a region generally longitudinally medial of said conductive elements, said outer electrically conductive element *terminating at said region, and said inner electrically conductive element extending beyond said region and being uninsulated at least at the distal end portion thereof for transmission of said electrical energy to said muscle tissue* [beyond said region being an electrical communication with said inner electrically conductive element, said inner and said outer elements being uninsulated at least at the distal end portions thereof].

5. Apparatus defined in claim 4 wherein said inner electrically conductive element comprises an electrode fabricated of a flexible material and wherein said outer electrically conductive element comprises at least one coil spring fabricated of an extremely flexible and resilient material.

6. Apparatus defined in claim 5 wherein said coil spring is constructed and arranged to define an outer and an auxiliary outer electrode and said outer and auxiliary outer electrodes are *insulated and* separated from one another but affixed together at said region by a joint fabricated of dielectric material.

7. Apparatus defined in claim 6 wherein a sleeve is positioned about said outer and auxiliary outer electrodes for protecting the joint at said region by precluding excessive flexing at that location.

8. Apparatus defined in claim 7 wherein a plurality of spaced apart markers is positioned upon said outer electrodes.

9. Apparatus defined in claim 8 wherein an impulse generator of any suitable and conventional construction is connected to said outer and to said auxiliary outer electrodes across the joint at said region.

10. Apparatus defined in claim 9 wherein said sleeve is movable longitudinally of said outer and auxiliary outer electrodes for removal therefrom and comprises an interior recess that defines a shoulder adapted to abut against the joint at said region for precluding movement of the sleeve beyond that location.

11. Apparatus defined in claim 9 wherein said sleeve is affixed to said outer and auxiliary outer electrodes at said region.

12. Method of artificially stimulating a heart that has stopped beating by transmitting thereto electrical impulses comprising at least the steps of, inserting a needle of any suitable and conventional construction having a sleeve portion, a hub portion and a needle portion through the chest wall of the body until the needle passes through the ventricular wall of the heart; removing the needle portion from the sleeve portion of the needle; inserting bi-polar extremely flexible and resilient cardiac apparatus having first and second spaced apart markers through the sleeve portion of the needle until a first marker thereof is disposed at the hub of the sleeve portion to indicate that the tip of the cardiac apparatus has just emerged from the sleeve portion at its tip; continuing the movement of said cardiac apparatus into the sleeve portion of the needle until a second marker is disposed adjacent the hub of the sleeve portion of the needle to indicate that the tip of the cardiac apparatus has entered a ventricle of the heart near the endocardium; removing the sleeve portion from the body over the cardiac apparatus; and connecting an impulse generator of any suitable and conventional construction across the cardiac apparatus at the poles thereof.

13. Method of artificially stimulating a heart that has stopped beating by transmitting thereto electrical impulses, comprising at least the steps of:

inserting a needle having a sleeve portion and a needle portion through the chest wall of the body until it enters the ventricular wall of the heart;

removing the needle portion from the sleeve portion of the needle;

inserting bi-polar extremely flexible and resilient cardiac apparatus having a removable sleeve through the sleeve portion of the needle until the tip thereof enters either the right or left ventricle of the heart near the endocardium;

removing the sleeve from the cardiac apparatus;

removing the sleeve portion of the needle from the body over the cardiac apparatus;

returning the sleeve of the cardiac apparatus to a position thereupon; and connecting an impulse generator of any suitable and conventional construction across the cardiac apparatus.

14. Method of artificially stimulating a heart that has stopped beating by transmitting thereto electrical impulses, comprising at least the steps of, inserting a needle of any suitable and conventional construction having a sleeve portion, a hub portion and a needle portion through the chest wall of the body until the needle passes through the ventricular wall of the heart; removing the needle portion from the sleeve portion of the needle; inserting bi-polar extremely flexible and resilient cardiac apparatus through the sleeve portion of the needle a distance such that the tip of the cardiac apparatus has just emerged from the sleeve portion at its tip; continuing the movement of said cardiac apparatus into the sleeve portion of the needle a further distance such that the tip of the cardiac apparatus has entered a ventricle of the heart near the endocardium; removing the sleeve portion from the body over the cardiac apparatus; and connecting an impulse generator of any suitable and conventional construction across the cardiac appaartus at the poles thereof.

(References on following page)

References Cited

The following references, cited by the Examiner, are of record in the patented file of this patent or the original patent.

UNITED STATES PATENTS

| | | | |
|---|---|---|---|
| 2,949,910 | 8/1960 | Brown et al. | 128—2.05 |
| 3,087,486 | 4/1963 | Kilpatrick | 128—404 X |
| 3,216,424 | 11/1965 | Chardack | 128—418 |
| 3,244,174 | 4/1966 | Wesbey et al. | 128—418 |

OTHER REFERENCES

Lillehei et al.: "Surgery," vol. 56, No. 3, September 1964, p. 468.

WILLIAM E. KAMM, Primary Examiner

U.S. Cl. X.R.

128—419 P